United States Patent [19]

Pawloski

[11] Patent Number: 4,885,381

[45] Date of Patent: Dec. 5, 1989

[54] PHOSPHATE-PHOSPHITES ACID HALIDES

[75] Inventor: Chester E. Pawloski, Bay City, Mich.

[73] Assignee: The Dow Chemical Company, Midland, Mich.

[21] Appl. No.: 179,793

[22] Filed: Apr. 11, 1988

Related U.S. Application Data

[62] Division of Ser. No. 849,590, Apr. 8, 1986, Pat. No. 4,755,547.

[51] Int. Cl.$^4$ ................................................ C07F 9/14
[52] U.S. Cl. ..................................... 558/155; 558/91; 558/140
[58] Field of Search .......................... 558/155, 140, 91

[56] References Cited

U.S. PATENT DOCUMENTS

| | | |
|---|---|---|
| 3,192,242 | 7/1965 | Birum . |
| 3,423,486 | 7/1969 | Ratz . |
| 3,707,586 | 6/1972 | Turley . |
| 3,812,208 | 10/1974 | Esser et al. . |
| 3,867,320 | 4/1975 | Gambardella et al. . |
| 3,906,061 | 5/1975 | Boyer . |
| 3,998,764 | 7/1976 | Vollmer et al. . |
| 4,133,846 | 8/1979 | Albright . |
| 4,281,097 | 9/1981 | Albright . |
| 4,298,709 | 10/1981 | Ginter et al. . |
| 4,510,101 | 7/1985 | Pawloski . |

OTHER PUBLICATIONS

California 117 Test, California Technical Bulletin 117, State of California, Department of Consumer Affairs, Bureau of Home Furnishings, North Highlands, California (Jan. 1980).
ANSI/ASTM D—2863—77 (ASTM American National Standard).
ANSI/ASTM E—84, (American National Standard).

*Primary Examiner*—Anton H. Sutto
*Attorney, Agent, or Firm*—Barbara J. Sutherland

[57] ABSTRACT

Included are halogenated phosphate-phosphites and their acid halides and acids. The halogenated phosphate-phosphites can be prepared by a process comprising serially contacing
 (A) a phosphorus trihalide with a triol;
 (B) a halogenating agent; and
 (C) an oxirane or an alcohol;
under conditions sufficient to prepare the halogenated phosphate-phosphite. Steps (A) and (B) can prepare their acid halides. Use of water in step (C) can prepare their acids. For example, 3-((bis(2-chloroethoxy)phosphino)oxy)(2-bromoethyl-2-methylpropyl, 2-bromoethyl, 2-chloroethyl)phosphorate can be prepared from 2-methyl-2-(hydroxymethyl)-1,3-propanediol; phosphorus trichloride; bromine; and ethylene oxide.

Also included is use of the compounds as a hyraulic fluid or flame retardant. For example, polyurethanes can be rendered less flammable with the halogenated phosphate-phosphite flame retardant.

6 Claims, No Drawings

PHOSPHATE-PHOSPHITES ACID HALIDES

CROSS-REFERENCE TO RELATED APPLICATION

This is a divisional, of application Ser. No. 849,590, filed Apr. 8, 1986, now U.S. Pat. No. 4,755,547.

FIELD

The invention concerns phosphorus compounds with a plurality of phosphorus atoms. The invention also concerns their preparation and use. The use can additionally concern hydraulic fluids, and flame-retardant compositions in which said phosphorus compounds are employed and their preparation.

BACKGROUND

Certain useful halogenated phosphates with a plurality of phosphate moieties are known. See, e.g., Birum, U.S. Pat. No. 3,192,242 (1965); Ratz et al., U.S. Pat. No. 3,423,486 (1969); Turley, U.S. Pat. No. 3,707,586 (1972); Esser et al., U.S. Pat. No. 3,812,208 (1974); Gambardella et al. U.S. Pat. No. 3,867,320 (1975); Vollmer et al., U.S. Pat. No. 3,998, 764 (1976); Albright, U.S. Pat. Nos. 4,133,846 (1979) and 4,281,097 (1981).

Certain other useful halogenated phosphorus ester compounds with a plurality of other phosphorus(V) moieties are known. For example, certain halogenated bis(phosphonate)s, useful as flame retardants for polyurethanes, are disclosed by Pawloski et al., U.S. Pat. No. 4,510,101 (1985).

Certain useful phosphorus compounds with a plurality of phosphorus (III) moieties are known. For example, certain halogenated bis(phosphite)s useful as fire retardants are disclosed by Boyer, U.S. Pat. No. 3,906,061 (1975).

What is lacking and what is needed are useful halogenated phosphorus compounds with a plurality of phosphorus moieties having different phosphorus oxidation states therein. What is additionally lacking are compositions having such a halogenated phosphorus compound employed therein.

SUMMARY

In one aspect, the invention comprises halogenated phosphate-phosphites and their acid halides and acids. Another aspect of the invention is a process to prepare a halogenated phosphate-phosphite comprising serially contacting
(A) a phosphorus trihalide with a triol;
(B) a halogenating agent; and
(C) an oxirane or an alcohol;
under conditions sufficient to prepare the halogenated phosphate-phosphite, a process to prepare an acid of a halogenated phosphate-phosphite comprising employing water in said step (C) under conditions sufficient to prepare the acid of a halogenated phosphate-phosphite and a process to prepare an acid halide of a halogenated phosphate-phosphite comprising serially contacting
(A) a phosphorus trihalide with a triol; and
(B) a halogenating agent
under conditions sufficient to prepare the acid halide of a halogenated phosphate-phosphite. Thus, the acid halides of halogenated phosphate-phosphites are useful in preparing the halogenated phosphate-phosphites and the acids of a halogenated phosphate-phosphite. These acid halides and acids are also useful flame retardants.

Often, the acids are generally useful in or as a hydraulic fluid.

An additional aspect of the invention is use of the halogenated phosphate-phosphites (etc.) as a hydraulic fluid or flame retardant. The hydraulic fluid use comprises transferring pressure with the halogenated phosphate-phosphite. The flame-retardant use comprises contacting an otherwise more flammable organic material with the halogenated phosphate-phosphite or an acid halide or acid thereof under conditions sufficient to lower the combustibility of the otherwise more flammable organic material, for example, an otherwise more combustible hydraulic fluid, or, polyurethanes. Thus, a further aspect of the invention is a flame-retardant composition comprising an otherwise more flammable organic material incorporated therewith a flame-retardant amount of a halogenated phosphate-phosphite.

ILLUSTRATIVE EMBODIMENTS

In general, the halogenated phosphate-phosphites are compounds which contain both a phosphate moiety and a phosphite moiety; whereby the valence available for further bonding in each of these required phosphate and phosphite moieties is three, and wherein the valence available for further bonding in both of these required phosphate and phosphite moieties is taken fully up (i.e., is saturated) with bonds to up to five (and preferably, five) separate organic moieties. Also, at least one (and preferably, one) of the organic moieties contains halogen selected from the group consisting of fluoro (F), chloro (Cl), bromo (Br) and iodo (I) (i.e., a halo-organic moiety) and is bonded to both of the required phosphate and phosphite moieties (i.e., bridging halo-organic moiety; hence, the corresponding hyphen in the compound nomenclature of the halogenated phosphate-phosphites herein). The phosphate moiety can be represented by the formula:

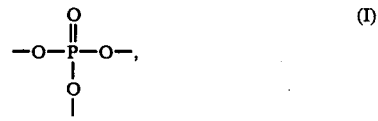

and the phosphite moiety can be represented by the formula:

Preferably, the organic moieties which are not the required bridging halo-organic moiety of the halogenated phosphate-phosphites are also halo-organic moieties. Preferably, in sum, at least five halo moieties are present in the halo-organic moieties, and only one bridging halo-organic moiety contains as few as one of the halo moieties. Preferred halo moieties are fluoro, chloro and bromo.

Preferably, the halogenated phosphate-phosphites contain a maximum of about a hundred carbons. A minimum of about ten carbons is also preferred.

Preferably, the halo-organic moieties, in addition to the required halogens and carbon, contain hydrogen or elements such as nitrogen, oxygen, sulfur and may include additional halogen. More preferably, the additional elements of the halo-organic moieties are hydrogen or oxygen, especially, hydrogen. Additional functionality which can be in the halo-organic moieties can be associative and derivative.

The associative additional functiionality is a functionality such as hydro (i.e., —H); cyano (i.e., —CN); ether (i.e., —O—Q, wherein Q is separately another carbon containing portion of the halo-organic moiety to which the oxy moiety, or other moiety as appropriate herein, is bonded through carbon); thioether (i.e., —S—Q); sulfoxy (i.e., —S($O_2$)—), acyl ester (i.e., —C(O)OQ); acyl thioester (i.e., —C(O)SQ); and thioacyl ester (i.e., —C(S)OQ). Thus, the associative functionality is one which can generally be present in the triol or oxirane or alcohol employed to prepare the halogenated phosphate-phosphite and remain present in the halogenated phosphate-phosphite prepared by the method of the invention (i.e., is generally inert). And thus, the associative functionality is such that it can generally remain associated with the triol or oxirane residue in the halogenated phosphate-phosphite (and hence, "associative"). However, the associative functionality may be also considered "derivative".

The derivative additional functionality is a functionality which can generally be incorporated into the halo-organic moieties such as after preparation of the halogeanted phosphate-phosphite. For example, hydroxyl functionality can be incorporated into the organic moieties by incorporating the associative moiety such as a dealkylatable alkoxy moiety, for example, (tert-butyloxy)methyl (i.e., $(CH_3)_3C$—O—$CH_2$—) and subsequently dealkylating it such as with phosphoric acid or an arylsulfonic acid preferably such as by employment of an oxirane such as tert-butyl glycidyl ether such as disclosed by Pawloski et al., U.S. Pat. No. 4,496,494 (1985) (incorporated herein by reference). Or, halo moieties can be incorporated into the organic moieties by halogenating unsaturated carbon to carbon bonds such as double bonds (i.e., C═C).

Preferably, the bis(phosphorus) halogenated phosphate-phosphites are compounds of the general formula

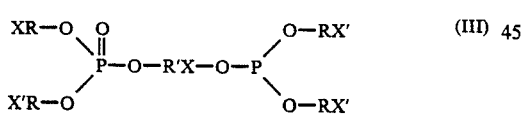

wherein
the XR and X'R (including the RX') moieties are separately at each occurrence halo-organic, preferably $C_{2-20}$ (i.e., from 2 to about 20 carbons) halo-organic;
the R'X moiety is the bridging halo-organic, preferably $C_{2-20}$ halo-organic;
X is separately at each occurrence halogen as halo selected from the group consisting of fluoro, chloro, bromo and iodo, preferably X';
X' is separately at each occurrence F, Cl or Br, preferably Cl or Br; and
R and R' may contain additional halogen.
In addition, it is preferred that the halo-organic (including the bridging) moieties are composed of elements selected appropriately from carbon, halogen, oxygen, hydrogen and nitrogen, more preferably from carbon, fluorine, chlorine, bromine, oxygen and hydrogen. Additionally preferred is an upper limit of carbon in the halo-organic moieties, separately at each occurrence, of about 10 carbons.

In general, the halogenated phosphate-phosphite acid halides are compounds which contain both the phosphate and phosphite moieties and have, in sum, from one to four (and preferably, four) appropriate halogens substituted for oxygen on the phosphorus atom and which contain at least one bridging halo-organic moiety. The acid halide of the phosphate in the acid halide of the halogenated phosphate-phosphite acid halides can be represented by the formula:

and the acid halide of the phosphite in the acid halide of the halogenated phosphate-phosphite acid halides can be represented by the formula:

wherein
Z is halido (F, Cl, Br, I) or an organic moiety, preferably a $C_{2-20}$ organic moiety, including organic moieties which are connected through singly bonded oxygen to the phosphorus, and preferably Z';
Z' is separately at each occurrence Z wherein the halido moiety is selected from the group consisting of fluorido, chlorido and bromido; and
in the acid halide of the halogenated phosphate-phosphite at least one of the sum of Z and Z' moieties is halido.

Preferably, the acid halides of the halogenated phosphate-phosphites are bis(phosphorus) acid halide compounds of the general formula:

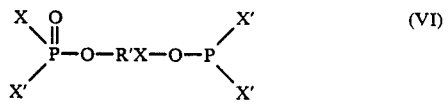

wherein
X is separately at each occurrence halogen, as halido, preferably X';
X' is separately at each occurrence fluorido, chlorido or bromido, more preferably chlorido or bromido; and
R'X is the bridging halo-organic moiety such as with the halogenated phosphate-phosphites.

The acids of a halogenated phosphate-phosphite can be considered to be such as an acid halide of a halogenated phosphate-phosphite in which, in sum, from one to four (and preferably, four) hydroxyl groups are bonded to the phosphorus atoms. Thus, the Z and Z' moieties can be additionally —OH, provided that in the acid, at least one of the sum of Z and Z' moieties is —OH.

Preferably, the acids of a halogenated phosphate-phosphite are bis(phosphorus) acid compounds of the general formula:

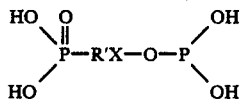
(VII)

wherein R'X is the bridging halo-organic moiety such as with the halogenated phosphate-phosphites, and X is F, Cl, Br or I.

The first step (A) in preparing the halogenated phosphate-phosphites and their acid halides and acids involves contacting the phosphorus trihalide with the triol. Conditions are preferably sufficient to prepare a cyclic intermediate with one acyclic and one heterocyclic phosphite acid halide.

The triol employed in the preparation of the halogenated phosphate-phosphites and their acid halides is an organic compound containing three hydroxy moieties. Preferably, the triol is otherwise generally inert in relation to the phosphorus trihalide. Thus, the triol can contain, for example, the associative moieties such as, for example, halo, cyano, ether, thioether, sulfoxy and acyl ester.

Preferably, two of the three hydroxy moieties of the triol are positioned in a manner which can allow formation of a five- to seven-membered heterocyclic phosphorus-containing ring with intermediate species. Of these heterocyclic rings, five- and six-membered rings are preferred.

The triol itself can be acyclic or cyclic. Preferably, the two hydroxy moieties which can allow the intermediate species ring formation are bonded to an acyclic part of the triol. More preferably, each hydroxy moiety of the triol is bonded to an acyclic part of the triol. Most preferably, the triol is acyclic.

The triol can be saturated or unsaturated. Most preferably, the triol is saturated. Exemplary triols include 1,2,3-propanetriol; 1,2,4-butanetriol; 1,2,10-decanetriol, 2,2-bis(hydroxymethyl)-1-octanol and 2-methyl-2-(2-hydroxyethoxy)methyl-1,3-propanediol.

Preferred triols include triols such as those of the general formula:

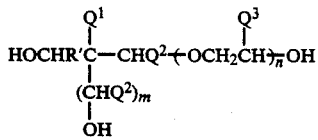
(VIII)

wherein
$Q^1$ is H or $C_{1-4}$ alkyl;
$Q^2$ is H or methyl;
$Q^3$ is H, $C_{1-4}$ alkyl or $C_{1-4}$ haloalkyl;
m is an integer from zero to two; and
n is an integer from zero to about five; and preferably therein
$Q^2$ is H;
m is 0 or 1; and optionally
n is from 1 to 4.

The triols can be obtained commercially or can be prepared by known methods such as reaction of a lower molecular weight triol with an oxirane. One preferred oxirane for this reaction is tert-butyl glycidyl ether. Naturally occurring cyclic carbohydrates can be employed, blocking any undesired free hydroxyl groups which may be present by known methods such as by O-methylation with methanol catalyzed with acid. A preferred method of preparing the triols of the formula (VIII) is by reaction of a corresponding lower molecular weight triol (e.g., 2-(hydroxymethyl)-1,3-propanediol)) with a ketal (e.g., dimethoxypropane) or acetal in the presence of an acid catalyst such as p-toluenesulfonic acid or polyphosphoric acid such as disclosed in copending U.S. application Ser. No. 799,777, filed Nov. 20, 1985, (incorporated herein by reference).

The triol can thus be a β-neocarbyltriol (e.g., m=1; n=0 in formula (VIII)). The β-neocarbyltriol contains a β-neocarbyl moiety hydroxylated with three hydroxy moieties. The β-neocarbyltriol is preferably a triol of the general formula (IX)    $Q^4H_2C-C(CH_2OH)_3$ 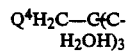

wherein $Q^4$ is hydrogen, halo, $C_{2-10}$ (i.e., from 2 to about 10 carbons) alkyl or $C_{2-10}$ haloalkyl. Exemplary β-neocarbyltriols include 2,2-bis(hydroxymethyl)-1-octanol and 2,2,-bis(hydroxymethyl)-1-propanol.

The phosphorus trihalide employed can contain halides of fluoride, chloride and bromide. The phosphorus trihalide is preferably a compound such as phosphorus trifluoride, phosphorus trichloride and phosphorus tribromide. Preferred halides of the phosphorus trihalide are chloride and bromide. Phosphorus trichloride is the most preferred phosphorus trihalide.

Preferably, about one molar equivalent of the triol is added in portions to about 2 molar equivalents of the phosphorus trihalide at room temperature (e.g., about 25° C.) or below (e.g., ice water bath). Higher temperatures typically produce undesired by-products. If the phosphorus trihalide is added to the triol, even at cold temperatures, considerable amounts of by-products are typically produced, and thus, it s preferred to slowly add the triol to the phosphorus trihalide.

The halogenating agent of step (B) is a suitable source of halogen (other than the phosphorus trihalide), which is imparted to the reaction mixture to prepare the halogenated phosphate-phosphite. Suitable halogenating agents of step (B) impart halogens, preferably fluorine, chlorine, bromine or iodine such as fluorido, chlorido, bromido or iodido moieties, or fluoro, chloro, bromo or iodo moieties. The halogenating agent can be a halogen-containing compound such as elemental fluorine, elemental chlorine, elemental bromine and elemental iodine and mixed halogen-containing compounds, for example, bromine chloride. Halogenating agents can also be organic halogenating agents. Organic halogenating agents such as N-bromosuccinimide, for example, can be employed as an organic brominating agent.

The halogenation is generally exothermic, and it is preferably carried out at room temperature or below. Higher temperatures typically produce a by-product of halogenated alkanes. Preferably, about two atomic equivalents of halogenating agent are employed in step (B) per mole of intermediate formed in step (A). Thus, for example, about one molar equivalent of elemental bromine is preferably employed in step (B) to supply about two atomic equivalents of bromine.

Preferably, the halogenating of step (B) is thus carried out under the conditions sufficient to prepare the acid halide of a halogenated phosphate-phosphite, which may be isolated and purified if desired. The contact with an oxirane or an alcohol subsequent to step (B) can prepare the halogenated phosphate-phosphites.

The oxiranes employed can include an alkyl epoxide such as ehtylene oxide, propylene oxide, 1,2- and trans-2,3-epoxybutane, 1,2-epoxydecane and 1,2-epoxyoctadecane; an unsaturated ether epoxide such as allyl glycidyl ether; a dealkylatable epoxide such as tert-butyl glycidyl ether; and a halogenated epoxide such as epifluorohydrin, epichlorohydrin and epibromohydrin. Also, oxiranes such as cis-7,8-epoxy-2-methyloctadecane; exo-2,3-epoxynorbornane; 3,4-epoxy-1-butene; 1,2-epoxy-7-octene; 1,2-epoxy-5,9-cyclododecadiene; 1,2-epoxy-3-phenoxypropane; 2,3-epoxypropyl-4-methoxyphenyl ether; 2,4,6-tribromophenol glycidyl ether; even oxiranes such as ethylene glycol diglycidyl ether, can be employed. However, the polyfunctional oxiranes such as the latter may produce undesired polymerization.

The halogenated phosphate-phosphite containing a residue of an unsaturated epoxide is preferably itself subsequently halogenated with the suitable halogenating agents. The elemental halogenating agents, especially bromine, are preferred. Temperatures are preferably cold (e.g., from about 0° C. to about 10° C.).

The halogenated phosphate-phosphite containing a residue of a dealkylatable epoxide is preferably dealkylated to obtain a hydroxylated-halogenated phosphate-phosphite of low viscosity. The dealkylation is preferably carried out with an acid such as phosphoric acid or an aryl sulfonic acid such as also disclosed by Ginter et al., U.S. Pat. No. 4,298,709 (1981) (incorporated herein by reference). The hydroxylated-halogenated phosphate-phosphites are preferably employed in rigid polyurethane foams.

The oxirane addition of step (C) is typically exothermic, most notably so in the presence of a catalytically effective amount of a catalyst such as a Lewis acid catalyst, for example, titanium tetrachloride, aluminum trichloride or aluminum tribromide. The oxirane reaction is preferably carried out at from room to elevated temperatures. Preferred elevated temperatures include temperatures of about 85° C., more preferably about 65° C. and most preferably about 45° C. Preferably, about four or more molar equivalents of the oxirane are employed in step (C). Less oxirane (and alcohol) can prepare the acid halide of halogenated phosphate-phosphite with less than four halide moieties.

The oxirane addition reaction is preferably carried out in the presence of the Lewis acid catalysts. For the most part, preferred amounts of the Lewis acid catalysts employed are from about 0.1 percent by weight of the intermediate formed in step (B) to about 5 percent by weight, most preferably about 0.5 percent by weight is employed.

The oxirane addition reaction of step (C) is preferred. Step (C) can also be carried out with an alcohol in the presence of an acid acceptor. Examples of suitable alcohols include aromatic alcohols such as phenol and benzyl alcohol; aliphatic alcohols such as methanol; ethanol; sec-butanol; 1-buten-4-ol and propargyl alcohol, and substituted alcohols such as 2-fluoroethanol; 2-chloroethanol; 2-bromoethanol; 2-iodoethanol; 2-cyanoethanol; 4-(4-methoxyphenyl)-1-butanol; tetrahydro-4H-pyran-4-ol; thiochroman-4-ol and 2-thiophenemethanol. Preferably, the alcohol contains a maximum of about 20 carbons. Alkyl alcohols are preferred, especially with a maximum of about 8 carbons, and more especially of from 2 to about 5 carbons. Monohydroxyl alcohols are also preferred.

The alcohol addition of step (C) is preferably carried out with about four or more molar equivalents of the alcohol based on the number of active hydrogens of the alcohol such as determined by the Zerewitnoff test (see e.g., Kohler et al., J. Am. Chem. Soc., 49, 3181–88 (1927)) per equivalent of the intermediate acid halide. For example, 1-pentanol has one active hydrogen, and about four or more moles of 1-pentanol are thus preferably employed per mole of the intermediate acid halide. A catalyst need not be present, however, the acid acceptor is preferably present. Examples of suitable acid acceptors include compounds such as pyridine and sodium carbonate. The acid acceptor is preferably added in the appropriate increments throughout the course of the alcohol addition.

Pressures of step (C), in general, are from ambient atmospheric to elevated, such as can be employed with gaseous reactants such as ethylene oxide and chlorine. The elevated pressures include pressures of about 50 psig (i.e., a gauge pressure of about 345 kPa). Preferably, the pressure is about ambient atmospheric pressure.

The water addition of step (C) to prepare the acid of a halogenated phosphate-phosphite is preferably carried out with from about one to four molar equivalents of water per equivalent of the intermediate acid halide, most preferably about four. The acid acceptor may also be present. Excess of an acid acceptor such as, for example, sodium carbonate can form corresponding (e.g., metallic) acid salts.

Preparations may be carried out neat or in the presence of a diluent. Preferably, an inert, liquid diluent is employed. Preferred inert, liquid diluents include the halogenated alkanes such as carbon tetrachloride, methylene chloride, chloroform and 1,2-dichloroethane.

The preparation is preferably carried out under an inert atmosphere such as argon and nitrogen. Nitrogen is preferred.

Purification of the halogenated phosphate-phosphites or their acid halides or acids can be by known methods such as by evaporation, distillation and chromatography. Distillation of the halogenated phosphate-phosphites is preferred.

The halogenated phosphate-phosphite and its acid can be produced in good yields. Preferably, yields are about 50 percent of theory or greater and most preferably about 70 percent of theory or greater. Yields of the acid halides of a halogenated phosphate-phosphite are thus preferably higher.

The following preferred sequence further illustrates the preferred process to prepare the halogenated phosphate-phosphites:

(A)

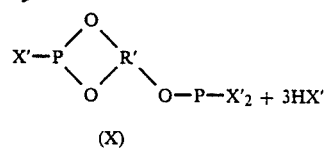

(X)

(B)

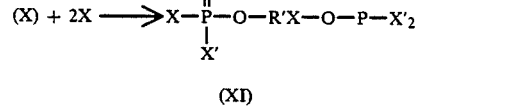

(XI)

-continued $$(XI) + 4\ R\overset{O}{\diagup} \longrightarrow \begin{matrix} XR-O & O & O-RX' \\ \diagdown & \parallel & \diagup \\ & P-R'X-O-P & \\ \diagup & & \diagdown \\ X'R-O & & O-RX' \end{matrix} \quad (C)$$

wherein
- R and R' are residues of the oxirane and triol, respectively, and R is preferably a $C_{2-10}$ (i.e., from 2 to about 10 carbons) oxirane;
- X is separately at each occurrence F, Cl, Br or I, preferably X';
- X' is separately at each occurrence F, Cl or Br, preferably Cl or Br;
- step (C) is catalyzed by the Lewis acid catalyst;
- the compound (X) is the acyclic and heterocyclic phosphite acid halide; and
- the compound (XI) is the acid halide of a halogenated phosphate-phosphite.

Steps (A) and (B) illustrate the preferred preparation of their preferred acid halides. Substitution of all or part of the oxirane of step (C) with the alcohols generally illustrates that preparation also.

Examples of the halogenated phosphate-phosphites include
- 3-((bis(2-chloroethoxy)phosphino)oxy)-2-(bromomethyl)-2-methylpropyl(2-bromoethyl)(2-chloroethyl)phosphate;
- 2-(((bis(2-chloropropoxy)phosphino)oxy)methyl)-2-(bromomethyl)butyl)2-bromopropyl)(2-chloropropyl)phosphate;
- 5-((bis(2-chloroethoxy)phosphino)oxy)-1-(bromomethyl)pentyl(2-bromoethyl)(2-chloroethyl)phosphate;
- 3-((bis(2,3-dichloropropoxy)phosphino)oxy)-2-(chloromethyl)-2-methylpropylbis(2,3-dichloropropyl)phosphate; and
- 3-((bis(2-chloroethoxy)phosphino)oxy)-2-(chloromethyl)-2-methylpropylbis(2-chloroethyl)phosphate.

Examples of the acid halides of a halogenated phosphate-phosphite include
- 3-((bis(chlorido)phosphino)oxy)-2-(bromomethyl)-2-methylpropylbromidochloridophosphate;
- 2-(((bis(chlorido)phosphino)oxy)methyl)-2-(bromomethyl)butylbromidochloridophosphate;
- 5-((bis(chlorido)phosphino)oxy)-1-(bromomethyl)pentylbromidochloridophosphate; and
- 3-((bis(chlorido)phosphino)oxy)-2-(chloromethyl)-2-methylpropylbis(chlorido)phosphate.

Examples of the acids of a halogenated phosphate-phosphite include
- 3-((bis(hydroxy)phosphino)oxy)-2-bromomethyl)-2-methylpropyl phosphoric acid;
- 2-((bis(hydroxy)phosphino)oxy)methyl-2-(bromomethyl)butyl phosphoric acid;
- 5-((bis(hydroxy)phosphino)oxy)-1-(bromomethyl)-pentyl phosphoric acid; and
- 3-((bis(hydroxy)phosphino)oxy)-2-(chloroemthyl)-2-methylpropyl phosphoric acid.

The halogenated phosphate-phosphite may have excellent viscosity. Preferably, the viscosity is measured with a Brookfield viscometer at 25° C. with a Number 6 spindle submersed with sample in a vial having a width at least 125 percent of the spindle diameter. The spindle is rotated at 100 rotations per minute (i.e., 100 rpm). Preferably, the Brookfield viscosity is about 10,000 centipoise (i.e., cP) or lower, more preferably about 5,000 cP or lower and most preferably about 2,000 cP or lower.

The halogenated phosphate-phosphite may have excellent thermal stability. A preferred measure of the thermal stability is by thermogravimetric analysis (i.e., TGA), where the sample tested is continuously monitored for weight loss as its temperature is progressively increased in an oven, under a nitrogen atmosphere. Preferably, the progressive temperature increase is at a rate of 20° C. per minute from an initial temperature of 20° C. with the sample size initially between 0.010 g and 0.020 g. Under these preferred test conditions, thermogravimetric analyses preferably have a 50 percent weight loss of sample (i.e., $TGA_{50}$) at a temperature of about 200° C. or above, more preferably about 250° C. or above and most preferably about 280° C. or above.

The thermogravimetric analysis at 10 percent weight loss (i.e., $TGA_{10}$) may be used also. The $TGA_{10}$ is otherwise measured as is the $TGA_{50}$. Preferred $TGA_{10}$ values include values found at about 160° C. or above, more preferably about 200° C. or above and most preferably about 230° C. or above.

Odor, especially in flame-retardant applications, may be improved by being reduced or even eliminated. The presence of a halogenated neopentane at levels of about 1 percent to about 4 percent by weight, can cause an odor. Keeping the presence of such a halogenated neopentane to levels below 1 percent by weight, more preferably 0.5 percent by weight, typically eliminates such an odor in the resulting flame-retardant product. The instant process typically avoids formation of such a halogenated neopentane and thus can contribute to a non-odoriferous flame-retardant product, especially with polyurethanes.

The halogenated phosphate-phosphite compounds can be employed as a hydraulic fluid or flame retardant. The preferred use of the halogenated phosphate-phosphites is as a flame retardant in polymeric materials, for example, polyurethanes. The preparation of the polymeric materials can be carried out by known methods. See e.g., the U.S. patents referenced herein.

As a flame retardant, the halogenated phosphate-phosphites are added in any amount which is effective to lower the combustibility of the otherwise more flammable organic material to any degree. By flame-retardant is meant that the halogenated phosphate-phosphite when incorporated in the more flammable organic material reduces the propensity of the more flammable organic material (e.g., polyurethane) to propagate combustion after the removal of a small scale ignition source such as a lit Bunsen burner.

Any amount of the phosphate-phosphite which is flame-retardant is suitable for this invention. Preferably, flame-retardant amounts of the halogenated phosphate-phosphite are from about one-half percent by weight to about 50 percent by weight of the otherwise more flammable organic material, for example, of polyahl of a polyurethane, most preferably between about 10 and 20 percent by weight.

One preferred method to measure this flame-retardant capability is an oxygen index (i.e., limiting oxygen index) measured by the oxygen demand test of ANSI/ASTM D-2863-77 (ASTM American National Standard) wherein the minimum concentration of oxygen in a mixture of dry $O_2$ and dry $N_2$ flowing upward, needed to cause combustion in a standard test column that will just support combustion under equilibrium conditions of candle-like burning is measured. Other conditions of the ANSI/ASTM D-2863-77 oxygen demand test include those set out in the ASTM American National Standard test (incorporated herein by reference).

Preferably, for ten appropriate A through D type (as in the D-2863-77 standard) specimens with the flame-retardant composition, the average limiting oxygen index (i.e., average LOI) is raised 10 percent or more, more preferably 20 percent or more and most preferably 30 percent or more, when measured either by time until extinguishing of the flame or distance of the burned specimen according to ASTM D-2863-77, when compared to ten otherwise comparable specimens without the flame-retardant halogenated phosphate-phosphite. It is also preferred that the average LOI of ten appropriate A through D type specimens is raised to above 21, more preferably to about 25 or above and most preferably, to about 30 or above. For example, specimens of a styrenic polymer resin such as resinous polystyrene and poly(acrylonitrile-butadiene-styrene) may have an average LOI of 18 before the incorporation of flame-retardant halogenated phosphate-phosphite and an average LOI of 25 afterward, which is a concurrent increase in average LOI of 39 percent; specimens of an alkylene polymer resin such as resinous polyethylene or polypropylene may have an average LOI of 17 before and 27 afterward; specimens of a polymer resin such as a polycarbonate may have an average LOI of 25 before and 32 afterward.

When incorporated into a rigid polyurethane foam, such as an insulating foam, preferred measures include the Steiner tunnel test of ANSI/ASTM E-84 of the ASTM National Standard test (incorporated herein by reference) or the equivalent such as Underwriter's Laboratories (i.e., UL) 723. It is preferred that the rigid foam pass the E-84 test or equivalent with a Class III rating or better, more preferably a Class II rating or better. It may be desired to incorporate into the flame-retardant polyurethane an amount effective to secure a Class I rating. Other tests such as the German DIN-4102-B2 test or its Swiss counterpart may be used.

When incorporated into a flexible polyurethane foam as a flame retardant, a preferred measure of the flame-retardant efficiency of the halogenated phosphate-phosphite is the Calif. 117 test such as in Calif. Technical Bulletin 117, State of Calif., Department of Consumer Affairs, Bureau of Home Furnishings, North Highlands, Calif. (Jan. 1980) (incorporated herein by reference). It is preferred that the Calif. 117 test is passed by the flame-retardant flexible foam composition.

To employ the halogenated phosphate-phosphite as a hydraulic fluid, one merely places the compound in a suitable solid boundried system and applies the requisite pressure. The halogenated phosphate-phosphite can be employed singly or in combination with other fluids such as oleaginous liquids (e.g., brake fluid). Because the halogenated phosphate-phosphite is preferably a flame retardant and preferably has high thermal stability, the oleaginous liquid-type hydrualic fluid can preferably be additionally rendered flame-retardant.

Specific Embodiments

The following examples further illustrate the invention. Percentages are by weight unless otherwise stated.

Example 1—Preparation of phosphoric acid: 3-((bis(2-chloroethoxy)phosphino)oxy), 2-(bromomethyl)-2-methylpropyl, 2-bromoethyl, 2-chloroethyl ester with the following general formula:

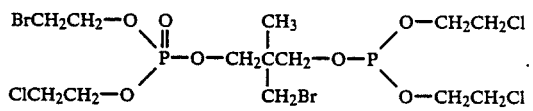

A. Preparation of the Acid Halide of the Halogenated Phosphate-Phosphite

Into a flask are placed 69 g (0.5 mole) of PCl₃ and 250 ml of methylene chloride. This mixture is cooled to 10° C. in an ice water bath, whereupon 30 g (0.25 mole) of 2-methyl-2-(hydroxymethyl)-1,3-propanediol is added in portions. Upon this addition, the mixture is allowed to warm to 40° C., and the flask is purged with nitrogen at reflux until hydrochloric acid ceases to evolve. The mixture is next cooled to 10° C. or lower in an ice water bath, whereupon 40 g of bromine in 50 ml of methylene chloride is added dropwise. Upon this addition, the mixture is allowed to warm to room temperature with stirring. The acid halide is of the general formula:

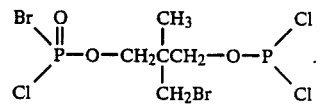

B. Preparation of the Halogenated Phosphate-Phosphite

Next 0.5 ml of TiCl₄ is added, and a solution of 50 g of ethylene oxide in 50 ml of methylene chloride is added dropwise. The resultant exotherm is controlled by maintaining the temperature of the mixture at 40° C. with a cold water bath. Upon completion of this addition, the mixture is refluxed for 30 minutes, and some low boilers are distilled off. Upon cooling to 20° C., 50 ml of dilute base is added, and the mixture is stirred for 10 minutes. The resulting product is filtered through filter cel, and the product layer is separated and filtered through some sodium sulfate, and low boilers are removed under reduced pressure at 80° C. to give 131 g of oil with Brookfield viscosity (Number 6 spindle; 100 rpm) of 250 cP at 25° C. at 85 percent theoretical yield. TGA: 225° C.; TGA₅₀: 276° C.; MW: 621.5 g per mole; Br: 25.7 percent; Cl: 17.1 percent; P: 10.0 percent.

Example 2—Preparation of phosphoric acid: 2-(((bis(2-chloropropoxy)phosphino)oxymethyl)-2-(bromomethyl)butyl, 2-bromopropyl, 2-chloropropyl ester with the following general formula:

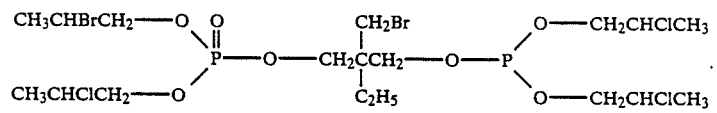

The procedure of Example 1 is followed employing the following: 69 g (0.5 mole) of $PCl_3$, 200 ml of 1,2-dichloroethane, 33.5 g (0.25 mole) of 2-ethyl-2-(hydroxymethyl)-1,3-propanediol, 40 g (0.25 mole) of bromine, 1 ml of $TiCl_4$ and 65 g (1.1 mole) of propylene oxide in 50 ml of 1,2-dichloroethane. An oil (120 g) with Brookfield viscosity (Number 6 spindle; 100 rpm) of 300 cP at 25° C. is obtained at 70 percent theoretical yield. $TGA_{10}$: 204° C.; $TGA_{50}$: 260° C.; MW: 691.5 g per mole; Br: 23.1 percent; Cl: 15.4 percent; P: 9.0 percent.

Example 3—preparation of phosphoric acid: 4-((bis(2-chloroethoxy)phosphino)oxy)-1-(bromomethyl)pentyl, 2-bromoethyl, 2-chloroethyl ester with the following general formula:

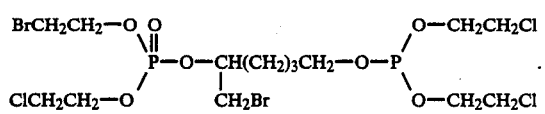

The procedure of Example 1 is followed employing the following: 69 g (0.5 mole) of $PCl_3$, 200 ml of methylene chloride, 33.5 g (0.25 mole) of 1,2,6-trihydroxyhexane, 40 g (0.25 mole) of bromine, 1 ml of $TiCl_4$ and 50 g (1.1 mole) of ethylene oxide in 50 ml of methylene chloride. An oil (116 g) with Brookfield viscosity (Number 6 spindle; 100 rpm) of 200 cP at 25° C. is obtained at 73 percent theoretical yield. $TGA_{10}$: 203° C.; $TGA_{50}$: 268° C.; MW: 635.5 g per mole; Br: 25.2 percent; Cl: 16.8 percent; P: 9.8 percent.

Example 4—Preparation of phosphoric acid: 3-((bis(2,3-dichloropropoxy)phosphino)oxy)-2-chloromethyl-2-methylpropyl, bis(2,3-dichloropropyl) ester with the following general formula:

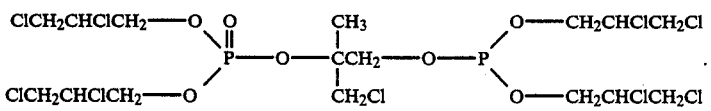

A. Preparation of the Acid Halide of the Halogenated Phosphate-Phosphite

Into a flask is placed 70 g (0.5 mole) of $PCl_3$. It is stirred and cooled to 10° C. in an ice water bath, whereupon 30 g (0.25 mole) of 2-methyl-2-(hydroxymethyl)-1,3-propanediol is added in portions. Next 250 ml of methylene chloride is added, and the mixture is slowly heated to 35° C. under a nitrogen blanket until hydrochloric acid ceases to evolve. The mixture is then cooled to 10° C., whereupon 18 g of chlorine is bubbled into the reaction mixture. Upon completion of the reaction, the acid halide is of the general formula:

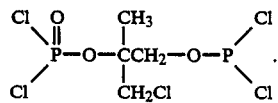

B. Preparation of the Halogenated Phosphate-Phosphite

Next 0.3 g of $AlCl_3$ is added, and 95 g (1.0 mole) of epichlorohydrin is added dropwise. An exothermic reaction occurs. The mixture is refluxed for 2 hours after this addition. The mixture is allowed to cool.

Then, 50 ml of 5 percent aqueous hydrochloric acid solution is added with stirring. The product layer is separated, and 50 ml of 5 percent aqueous NaOH solution is added with stirring. The product layer is separated and filtered, and the solvent is removed by distillation to give an oil (138 g) with Brookfield viscosity (Number 6 spindle; 100 rpm) of 950 cP at 25° C. at 76 percent theoretical yield. MW: 726.5 g per mole; Cl: 44 percent; P: 8.5 percent.

Example 5—Preparation of phosphoric acid: 3-((bis(2-chloroethoxy)phosphino)oxy)-2-chloromethyl-2-methylpropyl, bis(2-chloroethyl) ester with the following general formula:

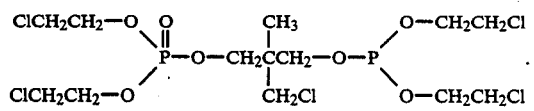

The procedure of Example 4 is followed employing the following: 140 g (1.0 mole) of $PCl_3$, 250 ml of methylene chloride, 60 g (0.5 mole) of 2-methyl-2-(hydroxymethyl)-1,3-propanediol, 36 g (0.5 mole) of chlorine, 1 g of $AlCl_3$ and 100 g (2.3 moles) of ethylene oxide in 100 ml of methylene chloride. An oil (177 g) with Brookfield viscosity (Number 6 spindle; 100 rpm) of 200 cP at 25° C. is obtained at 67 percent theoretical yield. MW: 532.5 g per mole; Cl: 33.3 percent; P: 11.6 percent.

I claim:

1. An acid halide of a halogenated phosphate-phosphite.

2. The acid halides of a halogenated phosphate-phosphite of claim 1 which correspond to a general formula:

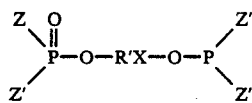

wherein
the R'X moiety is a bridging $C_{2-20}$ halo-organic moiety, wherein
X is selected from the group consisting of fluoro, chloro, bromo and iodo;
Z is halido selected from the group consisting of fluorido, chlorido, bromido and iodido, or $C_{1-20}$ organic; and
Z' is separately at each occurrence halido selected from the group consisting of fluorido, chlorido and bromido, or $C_{1-20}$ organic;
provided that at least one of the sum of Z and Z' moieties is halido.

3. The compound of claim 2 wherein Z and Z' are halido.

4. The compound of claim 3 wherein the halido moieties are selected from the group consisting of chlorido and bromido.

5. A process to prepare an acid halide of a halogenated phosphate-phosphite comprising serially contacting (A) a phosphorus trihalide with a triol; and (B) a halogenating agent, under conditions sufficient to prepare the acid halide of a halogenated phosphate-phosphite.

6. The process of claim 5 wherein the acid halide of a halogenated phosphate-phosphite corresponds to a general formula:

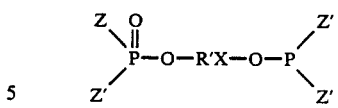

wherein
the R'X moiety is a bridging $C_{2-20}$ halo-organic moiety, wherein
X is selected from the group consisting of fluoro, chloro, bromo and iodo;
Z is halido selected from the group consisting of fluorido, chlorido, bromido and iodido, or $C_{1-20}$ organic; and
Z' is separately at each occurrence halido selected from the group consisting of fluorido, chlorido and bromido, or $C_{2-20}$ organic;
provided that at least one of the sum of Z and Z' moieties is halido.

* * * * *

UNITED STATES PATENT AND TRADEMARK OFFICE
CERTIFICATE OF CORRECTION

PATENT NO. : 4,885,381

DATED : December 5, 1989

INVENTOR(S) : Chester E. Pawloski

It is certified that error appears in the above-identified patent and that said Letters Patent is hereby corrected as shown below:

On the cover page, the following should be added to the references cited under U.S. PATENT DOCUMENTS:

| | | |
|---|---|---|
| 3,562,169 | 2/71 | Prentice |
| 3,725,510 | 4/73 | Dever et al. |
| 3,890,409 | 6/75 | Mayerhoefer et al. |
| 3,933,696 | 1/76 | Shim |
| 4,313,761 | 2/82 | Joyce III et al. |

On the cover page, the following should be added after the U.S. PATENT DOCUMENTS:

FOREIGN PATENT DOCUMENT 152,073          9/83          Japan

On the cover page in the ABSTRACT, lines 11-13, "3-((bis(2-chloroethoxy)phosphino)oxy)(2-bromoethyl-2-methylpropyl, 2-bromoethyl, 2-chloroethyl)phosphorate" should read -- 3-((bis(2-chloroethoxy)phosphino)oxy)-(2-bromomethyl-2-methylpropyl, 2-bromoethyl, 2-chloroethyl)phosphorate --.

On the cover page in the ABSTRACT, line 16, "hyraulic" should read -- hydraulic --.

UNITED STATES PATENT AND TRADEMARK OFFICE
CERTIFICATE OF CORRECTION

PATENT NO. : 4,885,381

DATED : December 5, 1989

INVENTOR(S) : Chester E. Pawloski

It is certified that error appears in the above-identified patent and that said Letters Patent is hereby corrected as shown below:

Col. 3, line 5, "functiionality" should read -- functionality --.

Col. 4, line 7, "atom" should read -- atoms --.

Col. 6, line 36, "s" should read -- is --.

Col. 7, line 2, "ehtylene" should read -- ethylene --.

Col. 9, the formula at the top of the column should read:

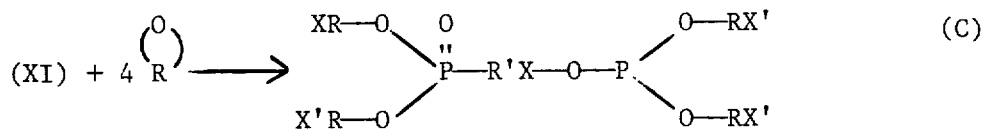

Col. 11, line 60, "hydrualic" should read -- hydraulic --.

Signed and Sealed this

Twenty-second Day of January, 1991

*Attest:*

HARRY F. MANBECK, JR.

*Attesting Officer*  *Commissioner of Patents and Trademarks*